United States Patent [19]

Kunz et al.

[11] Patent Number: 5,772,013
[45] Date of Patent: Jun. 30, 1998

[54] METHOD AND APPARATUS FOR PRODUCING DI- AND MORE HIGHLY OXIDIZED CARBOXYLIC ACIDS

[75] Inventors: Markwart Kunz, Worms; Andreas Schwarz, Plattling; Jörg Kowalczyk, Bockenheim, all of Germany

[73] Assignee: Sudzucker Akiengesellschaft Mannheim/Ochsenfurt, Mannheim, Germany

[21] Appl. No.: 749,092

[22] Filed: Nov. 14, 1996

[30] Foreign Application Priority Data

Nov. 14, 1995 [DE] Germany .................. 195 42 287.2

[51] Int. Cl.⁶ .................................................. B01D 61/44
[52] U.S. Cl. .................. 204/520; 204/522; 204/523; 204/530; 204/534; 204/537; 204/539; 204/541
[58] Field of Search .................................. 204/520, 522, 204/523, 530, 534, 537, 539, 541

[56] References Cited

U.S. PATENT DOCUMENTS

| | | | |
|---|---|---|---|
| 4,375,393 | 3/1983 | Reiff et al. | 204/79 |
| 4,976,893 | 12/1990 | Leupold | 260/413 |
| 5,238,597 | 8/1993 | Fritsche-Lange et al. | 252/174.18 |

FOREIGN PATENT DOCUMENTS

| | | |
|---|---|---|
| 0040709A1 | 12/1981 | European Pat. Off. |
| 0206054A2 | 12/1986 | European Pat. Off. |
| 0326673A2 | 8/1989 | European Pat. Off. |
| 35 35720 A1 | 4/1987 | Germany |
| 39 26642 A1 | 3/1990 | Germany |
| 43 07 388 A1 | 9/1994 | Germany |

OTHER PUBLICATIONS

Mehltretter, C.L., "D–Glucavic Acid," *Methods Carbohydr. Chem.* 2, 1963, pp.46–48 no month.
Challenger, et. al., "Formation of Organic Acids from Sugars by Aspergillus niger", *Nature 119*, 1927, p. 674 no month.
Röper, Harald, "Selective Oxidation of D–Glucose Chiral Intermediates for Industrial Utilization", *Starch/Stärke 42*, 1990, No. 9, pp. 342–349 no month.
Heyns, et al., "Selective Catalytic Oxidation of Carbohydrates, Employing Platinum Catalysts", *Adv. Carbohydr. Chem. 17*, 1962, p. 169 no month.
Edye, et al., "Platinum Catalysed Oxidation of Sucrose", *J. Carbohydrate Chemistry*, 10(1), 1991, p. 11 no month.
Kunz, Marwart et al., "Katalytische Oxidation von Isomaltulose", *Chem. Ing. Tech. 67*, No. 7, 1995, p. 836 no month.

*Primary Examiner*—Arun S. Phasge
*Attorney, Agent, or Firm*—Salter & Michaelson

[57] ABSTRACT

A method is disclosed for producing di- and more highly oxidized carboxylic acids from a compound selected from a first group consisting of carbohydrates, carbohydrate derivatives and carbohydrate derivatives having more than one primary alcohol group, comprising oxidizing, in an aqueous solution in a concentration between 0.1% and 60%, the compound selected from said first group and a compound selected from a second group consisting of monooxidized carbohydrates, monooxidized carbohydrate derivatives and monooxidized carbohydrate derivatives having more than one primary alcohol group, with one of oxygen and an oxygen-containing gas, on one of a noble metal catalyst and a mixed metal catalyst; electrodialyzing the oxidized compounds in at least one electrodialysis stage; and removing said di- and more highly oxidized carboxylic acids in said at least one electrodialysis stage.

13 Claims, 2 Drawing Sheets

METHOD AND APPARATUS FOR PRODUCING DI- AND MORE HIGHLY OXIDIZED CARBOXYLIC ACIDS

BACKGROUND OF THE INVENTION

The invention relates to a method for producing di- and more highly oxidized carboxylic acids in particular from carbohydrates, and carbohydrate derivatives with more than one primarily alcohol group. It further relates to an apparatus for carrying out the method.

Various methods of oxidizing carbohydrates selectively in two positions exist. For example, glucaric acid is obtained as aldaric acid by the oxidation of glucose with concentrated nitric acid. However, since such a reaction has to be conducted batchwise, only small yields of potassium hydrogen glucarate can be obtained [C. L. Mehltretter, D-glucavic Acid, in: Methods Carbohydr. Chem. 2 (1963), 46].

An *Aspergillus niger* strain is also described, which oxidizes D-glucose to D-glucarate [F. Challenger et al., Formation of organic acids from sugars by *Aspergillus niger*, in: Nature 119 (1927), 674]. Biotechnological methods, however, have some disadvantages. The breeding of the microorganisms or production of the biocatalysts is problematic, since pure cultures are required for bioreactors in most cases. It consequently often becomes necessary to operate the process in a sterile manner, which entails considerable equipment costs. Because of the genetic instability of microorganisms, it is frequently impossible on technical grounds to achieve a continuous production process.

Heterogeneously catalysed oxidation with noble metals of the 8th sub-group on suitable support materials represents a further possible method of obtaining dioxidized carbohydrates. In this method, the oxidation of D-glucose or of D-gluconic acid to D-glucaric acid with atmospheric oxygen takes place chemically, e.g., on Pt/C catalysts. The small selectivity with respect to glucaric acid is a disadvantage of this batchwise reaction procedure. The product mixture obtained is instead highly complex. Under optimized conditions the yield in potassium glucarate is only approx. 40% after crystallization [H. Roper, Selective oxidation of D-glucose: Chiral intermediates for industrial utilization, in: Starch/Starke 42 (1990), No. 9, 342–349].

Similar problems occur with the oxidation of saccharose. HEYNS and PAULSEN have already investigated this reaction on platinum catalysts [K. Heyns and H. Paulsen, Selective catalytic oxidation of carbohydrates, employing platinum catalysts, in: Adv. Carbohydr. Chem. 17 (1962), 169]. The product compositions were so complex in terms of chemical structures and compositions that more precise details could not be given.

More recent investigations [L. A. Edye et al., Platinum catalysed oxidation of sucrose, in: J. Carbohydr. Chem. 10(1) (1991), 11; C. Recker Dissertation, TU Braunschweig (1995)] have shown that the product mixture contains, in addition to the three possible monooxidation products, $C_{66}$-saccharose dicarboxylic and other non-identifiable substances.

A method for the catalytic oxidation of saccharose, described in German Patent document 35 35 720 Al, indicates that saccharose tricarboxylic acid is also to be found in the product mixture, together with other more highly oxidized products.

It is known from German Patent document 43 07 388 Al, that for the selective production of monocarboxylic acids from carbohydrates, carbohydrate derivatives or derivatives with more than one primary alcohol group, the starting materials must be fed to an oxidation reactor and connected in series to an electrodialysis unit, in which the monooxidation products are obtained. The non-oxidized substances are returned continuously into the oxidation reactor. The selectivity of the reaction with respect to monocarboxylic acid formation is excellent, however, di- or more highly oxidized carboxylic acids cannot be produced by this method.

SUMMARY OF THE INVENTION

The object of the invention is to provide an oxidation of carbohydrates and carbohydrate derivatives with more than one primary alcohol group with an improved selectivity regarding the di- and more highly oxidized products.

This object is achieved by the fact that carbohydrates, carbohydrate derivatives or derivatives with more than one primary alcohol group or monooxidized carbohydrates, and carbohydrate derivatives or derivatives with more than one primary alcohol, are oxidized continuously in aqueous solution in concentrations between 0.1 and 60%, with oxygen or oxygen containing gases on noble metal or mixed metal catalysts. The flow of the products so formed is passed to one or more electrodialysis stages connected in series and the di- and more highly oxidized carboxylic acids are removed and recovered there.

This method is exceptionally suitable for achieving the object. Use is made in the electrodialysis stages of a surprising effect: the method known from German Patent document 43 07 388 Al is, as already mentioned, provided for obtaining monocarboxylic acids. It also does this with a very high selectivity. Specialist circles have continued to assume to date, including in recent publications, that dicarboxylic acids could not be obtained or indeed recovered in the electrodialysis stages [M. Kunz et al., Catalytic oxidation of isomaltulose, in: Chem.Ing.Tech.67 (1995).No.7, 836].

However, if the monocarboxylic acids obtained with this method are not separated selectively, but instead are returned in large measure into the oxidation process, dicarboxylic acid portions, contrary to this current view, are obtained in this process, and the proportion is increased if the returning step is repeated continuously.

These dicarboxylic acid portions in particular can likewise be separated selectively with an electrodialysis stage. The use of electrodialysis for the recovery of acids from salts is certainly known, for example from German Patent document 3 926 642 Al, but not in the current area of application. In order to separate the dicarboxylic acid portions just mentioned, use is made of the surprising fact that the electrodialysis is capable, as a membrane separation method, of discriminating between mono and dianions, and between ions with different charge properties.

This method thereby becomes exceptionally suitable for the isolation and recovery of dicarboxylic acids. The di-acids formed can be removed from the oxidation cycle continuously and do not undergo any undesirable consequent reactions in the reaction cycle which would reduce the selectivity of the reaction in terms of di-acid formation. Continuous operation of the process is obtained by returning the mixture of monooxidation products and the carbohydrate used as educt to the oxidation stage. The addition of educt is regulated as a function of the extraction of dicarboxylic acids from the reaction cycle in such a way that the educt concentration remains constant. During this reaction procedure, the monocarboxylic acids occur as intermediate products, for which a stationary concentration is obtained in the reaction cycle.

A continuous method for the selective production of dicarboxylic acids is therefore obtained with the invention, the method being far superior in terms of selectivity and reaction procedure to the methods known to date for the production of dicarboxylic acids.

Di- or more highly functionalized saccharides or saccharide derivatives are of great interest industrially, first since they possess direct application possibilities because of their hydrophilic nature, their skin compatibility and their complex-forming properties, and second, since they can be processed by simple, technically feasible derivitizations to attractive products in the polymer and surfactant sector. Due to their ecologically positive properties, these products possess considerable advantages compared with known competing products which are based on petrochemicals.

The result of the method was particularly surprising because the technical method from German Patent document 43 07 388 Al is intended, in a directly contrary manner, to ensure that the dicarboxylic acid portions in an oxidation mixture from carbohydrates, carbohydrate derivatives or derivatives with more than one primary alcohol group, are limited as far as possible in favor of a selective monocarboxylic acid production, and this aim is also achieved to an extremely high degree. This result becomes possible because the return of the monoacid products leads to a very high intermediate product concentration level of monooxodized products being obtained, which consequently then lead in the final analysis to a dicarboxylic acid production.

For the recovery of the dicarboxylic acid, a voltage value is preferred in the electrodialysis stage which is far lower than the voltages used elsewhere in electrodialysis stages and in particular is also far lower than the value used to separate the monocarboxylic acids in the prior art according to German Patent document 43 07 388 Al. Experiments have shown and confirmed that, due to this very low voltage, a selection can take place precisely between the monocarboxylic acids and the dicarboxylic acids, i.e., the dicarboxylic acids can be filtered out. A voltage value of 0.1 to 4.9 volts has proved to be particularly suitable in the experiments. A higher value may be preferred if other types of membranes are used, since the important factor is the relative relationships with the voltages used for the separation of monocarboxylic acids, which are also higher for other types of membranes.

It is particularly preferable if several electrodialysis stages are connected one after the other. A considerable improvement in selectivity is achieved by this connection one after the other.

A further improvement and in particular an increase in the rate of dicarboxylic acid formation preferably takes place by the use of porous support materials or those with large specific surface for the catalysts.

An increase in the rate of dicarboxylic acid formation due to catalysts of this kind has also been confirmed experimentally. The desired dicarboxylic acid can also be produced by the catalysts preferred for the isolation of monocarboxylic acids. However, the higher formation rate is also of advantage for the more rapid or more selective recovery of the dicarboxylic acid after the electrodialysis stage.

BRIEF DESCRIPTION OF THE DRAWINGS

A preferred embodiment of the present invention will now be described in detail with reference to the accompanying drawings, wherein.

DESCRIPTION OF THE PREFERRED EMBODIMENT

Figure 1:
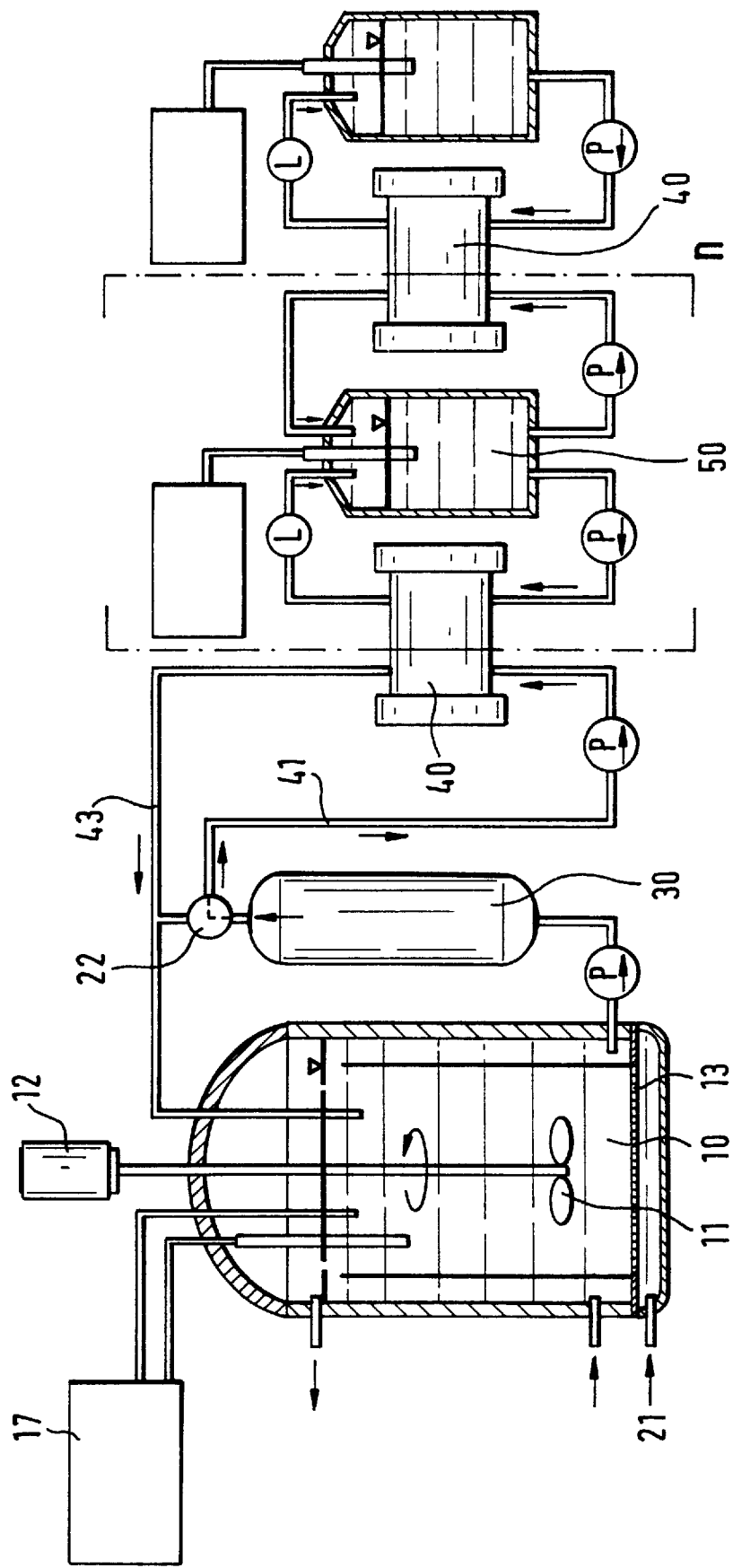
FIG. 1 shows a preferred embodiment of the invention.

Basically, the invention provides a method for producing di- and more highly oxidized carboxylic acids from carbohydrates, and carbohydrate derivatives or derivatives with more than one primary alcohol group, wherein carbohydrates, and carbohydrate derivatives with more than one primary alcohol group are oxidized continuously in aqueous solution in concentrations between 0.1% and 60%, and with oxygen or oxygen-containing gases on noble metal or mixed metal catalysts. The flow of the products so formed is passed to one or more electrodialysis stages connected in series and the di- and more highly oxidized carboxylic acids are removed and recovered there.

More specifically, a method for producing di- and more highly oxidized carboxylic acids from a compound selected from a first group consisting of carbohydrates, carbohydrate derivatives and carbohydrate derivatives having more than one primary alcohol group comprises the steps of:

oxidizing, in an aqueous solution in a concentration between 0.1% and 60%, said compound selected from said first group and a compound selected from a second group consisting of monooxidized carbohydrates, monooxidized carbohydrate derivatives and monooxidized carbohydrate derivatives having more than one primary alcohol group, with one of oxygen and an oxygen-containing gas, on one of a noble metal catalyst and a mixed metal catalyst;

electrodialyzing the oxidized compounds in at least one electrodialysis stage; and removing said di- and more highly oxidized carboxylic acids in said at least one electrodialysis stage.

An apparatus for carrying out the method comprises a series connection of a gassing stage, an oxidation stage, and a plurality of electrodialysis stages, as well as a return line from said electrodialysis stages to said gassing stage.

Referring to the embodiment, the catalytic oxidation of saccharose to the saccharose dicarboxylic acids will be specifically discussed.

The saccharose molecule possesses three primary hydroxy groups, which can all be oxidized for the carboxyl function. The carboxyl acids that can be derived from this are given below with their abbreviated names, which signify:

| | |
|---|---|
| $C_6$-saccharose monocarboxylic acid: | 2-0-(1-0-α-D-glucopyranosyl)-β-D-fructofuranuronic acid |
| $C_{6'}$-saccharose monocarboxylic acid: | 1-0-(2-0-β-D-fructofurannosyl)-α-D-glucopyranuronide |
| $C_1$-saccharose monocarboxylic acid: | 2-0-1-0-α-D-glucopyranosyl)-β-D-arabino-2-hexulofuranonic acid |
| $C_{66'}$-saccharose dicarboxylic acid: | 1-0-2-0-β-D-glucopyranosyl)-β-D-arabino-2-hexulofuranaric acid |
| $C_{61}$-saccharose dicarboxylic acid: | 2-0-(1-0-α-D-glucopyransyl)-β-D-arabino-2-hexulofuranic acid |
| $C_{6'1}$-saccharose dicarboxylic acid: | 1-0-(2-0-β-D-arabino-2-hexulo-furanosonyl)-α-D-glucopyranur-onide |
| $C_{66'1}$-saccharose tricarboxylic acid: | 2-0-(1-0-α-D-glucopyranurony-1)-β-D-arabino-2-hexulofuranaric acid |

An aqueous saccharose solution is placed in an agitated vessel 10 having an agitator 11 and a motor 12. The aqueous saccharose solution is supplied with air through the fitted bottom and gassed at 21. The pH value is held at the desired value in the agitated vessel 10 by means of the pH control 17. After thorough mixing in the agitated vessel 10, the thermostatted, pH-controlled aqueous saccharose solution enriched with oxygen is passed by a pump labelled P to an oxidation stage 30, which in this example contains a Pt/C supported catalyst. The catalytic oxidation of the saccharose to the monocarboxylic acids takes place in this oxidation stage 30. The reaction mixture is then passed by the next pump P to an electrodialysis stage 40. A sufficiently low electrodialysis voltage is selected so that the monocarboxylic acids are not carried away, or are carried away far more slowly than the saccharose dicarboxylic acids. The monocarboxylic acids are enriched in the concentrate cycle along a path labelled 41. Due to the lowering of the electrodialysis voltage, a clear discrimination between mono- and dicarboxylic acids takes place. If the solution enriched with dicarboxylic acids in this way is eletrodialyed once again, a further enrichment of the dicarboxylic acids takes place. Depending on the enrichment, a sufficient number of electrodialysis stages can be connected in series so that the dicarboxylic acids are separated completely from the monocarboxylic acids.

The monocarboxylic acids are then, together with non-oxidized saccharose, pumped back again along the path 43 into the tank or the agitated vessel 10. From there, they are pumped into the oxidation stage 30 again after renewed intermixing, air enrichment, and pH control.

The continuous mode of operation of the apparatus is achieved by the fact that the educt is metered again according to the saccharose consumption, so that its concentration is virtually constant.

With the catalyst used here, the saccharose was oxidized more rapidly to the monocarboxylic acids than the monocarboxylic acids were to the diacids, and consequently, the monocarboxylic acids were enriched up to a particular stationary concentration in the reaction cycle. This concentration is dependant on the amount of catalyst used for the oxidation, on the membrane area available in the electrodialysis unit, and on the voltage applied.

In a tank 50, a product mixture which consisted of 56% saccharose monocarboxylic acids and 44% more highly oxidized derivatives was enriched. The main component of these more highly oxidized derivatives was C66'- saccharose dicarboxylic acid. The other two saccharose dicarboxylic acids ($C_{61}$- and $C_{6'1}$-saccharose dicarboxylic acid) each made up 7.5% of the product mixture. No secondary products were observed. The mixture obtained after the second electrodialysis stage already consisted of 75% of saccharose dicarboxylic acids. The discrimination between dicarboxylic acids and monocarboxylic acids in an electrodialysis stage is dependent to a high degree on the voltage applied. In a typical test, the saccharose dicarboxylic acids were enriched approximately three or four times as rapidly as the saccharose monocarboxylic acids.

In addition to the high selectivity of the oxidation with respect to the formation of dicarboxylic acids that can be achieved in this way—without this selectivity being reduced in a noticeable manner in the individual electrodialysis stages by the formation of secondary, consequent or decomposition products—a further conspicuous advantage of the method is that the catalyst does not deactivate even in a thirty-day long-term test.

It is possible to use, as an alternative to saccharose as the educt for dicarboxylic acid production, a mixture of the saccharose monocarboxylic acids. Such a mixture can be produced without difficulty by the method described for monocarboxylic acid production and used for dicarboxylic acid production without further purification. A continuous mode of operation is obtained in this case by repeating the metering of the monocarboxylic acid mixture according to consumption. In the case of saccharose dicarboxylic acid production, the rate of reaction proves to be immaterial whether saccharose or a mixture of saccharose monocarboxylic acids is used as educt. An investigation of the catalytic oxidation of palatinose performed batchwise without electrodialysis has shown, however, that the secondary oxidation of the monocarboxylic acid is inhibited by the educt of the primary reduction (H. Puke, Dissertation, TU Braunschweig, 1992). It is possible in this case to use the palatinose monocarboxylic acids as educts for the continuous palatinose dicarboxylic acid production, which leads to an increase in the rate of oxidation.

The possibility of such a method of operation—catalytic oxidation without electrodialysis unit—is also indicated in FIG. 1. In this regard, by reserving a three-way cock 22, the reaction solution is pumped back into the agitated vessel 10 directly after leaving the oxidation reactor 30.

Figure 2:
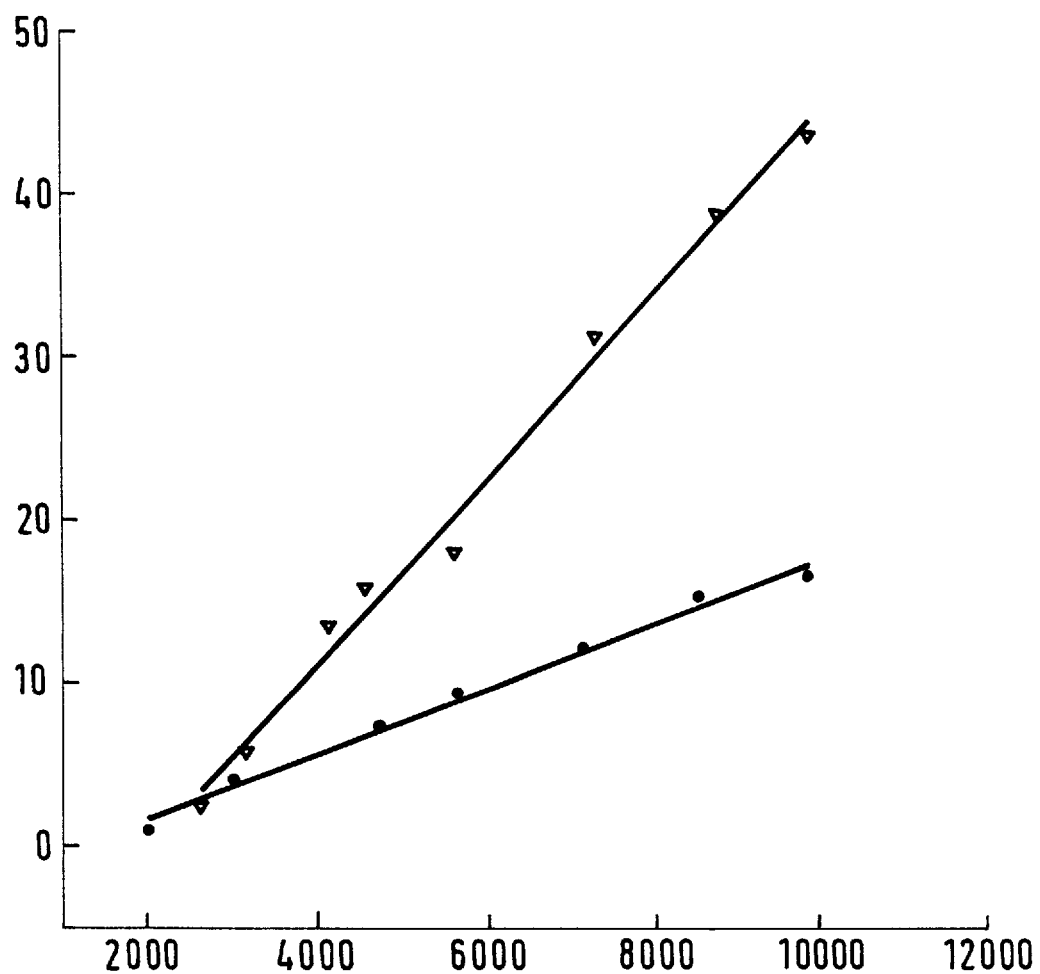
FIG. 2 shows a process flow chart for the embodiment.

It was found during the saccharose oxidation that the rate of the continuous di-acid production can be increased considerably, for example, by the selection of an activated carbon with a high specific surface compared with an activated carbon with small specific surface. FIG. 2 shows the increase over time in the $C_{66'}$-saccharose dicarboxylic acid as a function of two catalysts A and B used. On the vertical axis, the reaction time is plotted in minutes, and on the horizontal axis, the $C_{66'}$-saccharose dicarboxylic acid is plotted in mmol. The two catalysts are indicated by different symbols, namely catalyst A by black dots • and catalyst B by empty triangles ▽. Both the catalysts are Pt/C supported catalysts which have similar particle size distribution. The specific surface of activated carbons used as support materials differ however, with catalyst B having the greater specific surface.

The method for continuous dicarboxylic acid production, described by taking saccharose oxidation as an example, can be applied without difficulty to other carbohydrates and carbohydrate derivatives.

During the oxidation of D-glucose or D-gluconic acid, glucaric acid can likewise be enriched in the concentrate cycle by lowering of the electrodialysis voltage, preferably prior to the two monooxidation products, gluconic acid and glucuronic acid. The selectivity of the reaction with respect to glucaric acid is far higher than during the batchwise reaction procedure, since the glucaric acid is removed from the oxidation cycle before consequent reactions can occur.

The examples given show that the method for the continuous catalytic oxidation of carbohydrates, carbohydrate derivatives and derivatives with more than one primary alcohol group, with separation of the reaction products by means of electrodialysis, is suitable not only for monocarboxylic acid production, but can also be applied to selective dicarboxylic acid production after the changing of some operating parameters.

It is furthermore possible to discriminate between di- and tricarboxylic acids by further lowering the electrodialysis voltage. In an experiment, the saccharose dicarboxylic acids purified by multi-stage electrodialysis were oxidized at an electrodialysis voltage of 1.0 V. As a result, an enrichment of saccharose tricarboxylic acid took place in the concentrate cycle. The educt can be separated by multi-stage electrodialysis. The oxidation rate was, however, very slow with the catalyst used, and the formation of cleavage and decomposition products of the saccharose dicarboxylic acids was also observed.

EXAMPLE 1

Continuous Oxidation of Saccharose at 35° C.

In the apparatus described there were used in the oxidation cycle 40 g of platinum/activated carbon catalyst (1% Pt/C; particle size 40–100 μm, Degussa), through which 1500 ml of a 0.1 molar aqueous saccharose solution were pumped. The oxidation cycle corresponded to the diluate cycle of the electrodialysis. Distilled water was used for the concentrate cycle and 1M $Na_2SO_4$ as electrode rinse solution. The reaction temperature was held at 35° C. by means of a circulation thermostat. The gassing of the agitated vessel was set to 100 $cm^3$ $O_2$/min and 400 $cm^3$ $N_2$/min by means of rotameters. The pH set point in the dialysis cycle was maintained at pH 6.5 by titration of the acids obtained by means of 1M $K_2CO_3$. The electrodialysis (Bel 11, Berghof GmbH Labortechnik) was equipped with 6 AMV/CMV membrane pairs (effective membrane area=360 $cm^2$) and was operated at a voltage of 2.0 volts. The course of the reaction was monitored by HPLC measurements. The product spectrum, which was enriched in the concentrate, had the following composition:
Saccharose monocarboxylic acids: 56%
Saccharose dicarboxylic acids: 44%

The product mixture was freeze-dried; 60 g of it were dissolved in 500 ml of distilled water and electrodialysed once again at 2.0 volts. The product spectrum, which was enriched in the concentrate, had the following composition:
Saccharose monocarboxylic acids: 25%
Saccharose dicarboxylic acids: 75%

The electrodialysis was terminated with a diluate composition of:
Saccharose monocarboxylic acids: 92%
Saccharose dicarboxylic acids: 8%

EXAMPLE 2

Oxidation of saccharose in a similar manner to Example 1, with an electrodialysis voltage of 2.5 volt. The product mixture obtained had the following composition:
Saccharose monocarboxylic acids: 34%
Saccharose dicarboxylic acids: 66%

EXAMPLE 3

Oxidation of a mixture of the three saccharose monocarboxylic acids:
$C_6$-saccharose dicarboxylic acid: 44%
$C_6^1$-saccharose dicarboxylic acid: 36%
$C_1$-saccharose dicarboxylic acids: 20%
in a similar way to Example 1, with an electrodialysis voltage of 2.0 volts. The product mixture obtained had the same composition as in Example 1:
Saccharose monocarboxylic acids: 56%
Saccharose dicarboxylic acids: 44%

EXAMPLE 4

Continuous Oxidation of Na-D-gluconate

The oxidation of Na-D-gluconate took place in the apparatus described in Example 1, with the AMV membranes of the electrodialysis stack being replaced by AM3 membranes and the electrodialysis voltage being 1.3 V. The Na-D-gluconate concentration came to 0.1 mol/l, pH value and temperature were set at 8.5° and 35° C. respectively. The continuously obtained product solution had the following composition:
Gluconic acid: 60%
other monocarboxylic acids: 13%
glucaric acid: 27%

The selectivity of the reaction with respect to glucaric acid was therefore 68%. No glucaric acid was detected in the educt solution by NMR spectroscopy.

It will be understood that the above description of the present invention is susceptible to various modifications, changes and adaptations.

What is claimed is:

1. A method for producing di- and more highly oxidized carboxylic acids from a compound selected from a first group consisting of carbohydrates, carbohydrate derivatives and carbohydrate derivatives having more than one primary alcohol group, the method comprising the steps of:

oxidizing, in an aqueous solution in a concentration between 0.1% and 60%, said compound selected from said first group and a compound selected from a second group consisting of monooxidized carbohydrates, monooxidized carbohydrate derivatives and monooxidized carbohydrate derivatives having more than one primary alcohol group, with one of oxygen and an oxygen-containing gas, on one of a noble metal catalyst and a mixed metal catalyst;

electrodialyzing the oxidized compounds in at least one electrodialysis stage; and removing said di- and more highly oxidized carboxylic acids in said at least one electrodialysis stage.

2. The method according to claim 1, wherein after said removing step, said oxidizing step is repeated on remaining non- and monooxidized educts.

3. The method according to claim 1, wherein the electrodialyzing step is carried out with a voltage being in a range less than that necessary for the separation of monocarboxylic acids.

4. The method according to claim 1, wherein the electrodialyzing step is carried out with a voltage in a range between 0.1 volt and 7 volts.

5. The method according to claim 1, wherein, in said electrodialyzing step, one of ion-exchange and bipolar membranes are used.

6. The method according to claim 1, wherein said electrodialyzing step is conducted in more than one electrodialysis stages connected in series wherein, in each stage, the di- and more highly oxidized carboxylic acids are enriched.

7. The method according to claim 1, wherein said catalyst comprises one of porous support materials and materials with large specific surfaces.

8. The method according to claim 1, wherein said compounds of said first group are selected from a group consisting of saccharides, reducing saccharides and sugar alcohols, and the compounds of said second group are selected from the group consisting of monooxidized derivatives of saccharides, reducing saccharides and sugar alcohols.

9. The method according to claim 1, wherein one of water and a mixture of water and secondary alcohols are used as solvents for said compound selected from said first group and said compound selected from said second group.

10. The method according to claim 1, wherein said oxidizing and electrodialyzing steps are done in a pH range from 1 to 13.

11. The method according to claim 1, wherein said oxidizing step is done at a temperature between 0° C. and 80° C.

12. The method according to claim 1, wherein educts are used in concentrations between 3% and 20%.

13. The method according to claim 1, wherein alkalizing agents are used for setting a pH.

* * * * *